US00PP19456P2

(12) United States Plant Patent
Danziger

(10) Patent No.: US PP19,456 P2
(45) Date of Patent: Nov. 18, 2008

(54) ***ANGELONIA* PLANT NAMED 'DANGELON13'**

(50) Latin Name: *Angelonia angustifolia*
Varietal Denomination: DANGELON13

(76) Inventor: Gabriel Danziger, PO Box 24, Moshav Mishmar Hashiva, Beit Dagan (IL), 50297

( * ) Notice: Subject to any disclaimer, the term of this patent is extended or adjusted under 35 U.S.C. 154(b) by 0 days.

(21) Appl. No.: 12/008,654

(22) Filed: Jan. 11, 2008

(51) Int. Cl.
*A01H 5/00* (2006.01)

(52) U.S. Cl. ..... Plt./404

(58) Field of Classification Search ..... Plt./404
See application file for complete search history.

*Primary Examiner*—Annette H Para

(57) ABSTRACT

A new and distinct *Angelonia* cultivar named 'DANGELONI3' is disclosed, characterized by having light pink flowers, a compact, upright plant habit and early, continuous flowering. The new variety is a *Angelonia*, normally produced as an outdoor garden or container plant.

2 Drawing Sheets

Latin name of the genus and species: *Angelonia angustifolia.*

Variety denomination: 'DANGELONI3'.

BACKGROUND OF THE INVENTION

The new cultivar is a product of a planned breeding program, under the direction of the inventor, Gabriel Danziger. The objective of the breeding program was to produce plants of *Angelonia angustifolia* with compact habits. The seed parent is the unpatented, proprietary seedling variety referred to as *Angelonia angustifolia* 'AL-6-197.' The pollen parent is the unpatented, proprietary seedling variety referred to as *Angelonia angustifolia* 'AL-D-147.' The new variety was discovered on March 2006, by the inventor in a group of seedlings resulting from that crossing, in Moshav Mishmar Hashiva, Israel.

Asexual reproduction of the new cultivar 'DANGELONI3' by vegetative cuttings was performed at a commercial greenhouse in Moshav Mishmar Hashiva, Israel and has shown that the unique features of this cultivar are stable and reproduced true to type on successive generations.

SUMMARY OF THE INVENTION

The cultivar 'DANGELONI3' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'DANGELONI3.' These characteristics in combination distinguish 'DANGELONI3' as a new and distinct *Angelonia* cultivar:

1. Compact plant habit.
2. Small flowers compared to other commercial Angelonia varieties.
3. Light pink flower color.
4. Very upright habit.

Plants of the new cultivar 'DANGELONI3' are similar to plants of the seed parent, *Angelonia angustifolia* 'AL-6-197' in most horticultural characteristics, however, plants of the new cultivar 'DANGELONI3' are more compact.

Plants of the new cultivar 'DANGELONI3' are similar to plants of the pollen parent, *Angelonia angustifolia* 'AL-D-147' in most horticultural characteristics, however, plants of the new cultivar are more compact and product more branches. Additionally, flowers of 'DANGELONI3' are smaller and darker than the pollen parent.

Plants of 'DANGELONI3' are similar to the commercial variety *Angelonia* 'Serena Pink,' a seed produced variety, however, plants of 'DANGELONI3' are short, more compact and produce more branches.

BRIEF DESCRIPTION OF THE PHOTOGRAPH

Figure 1:
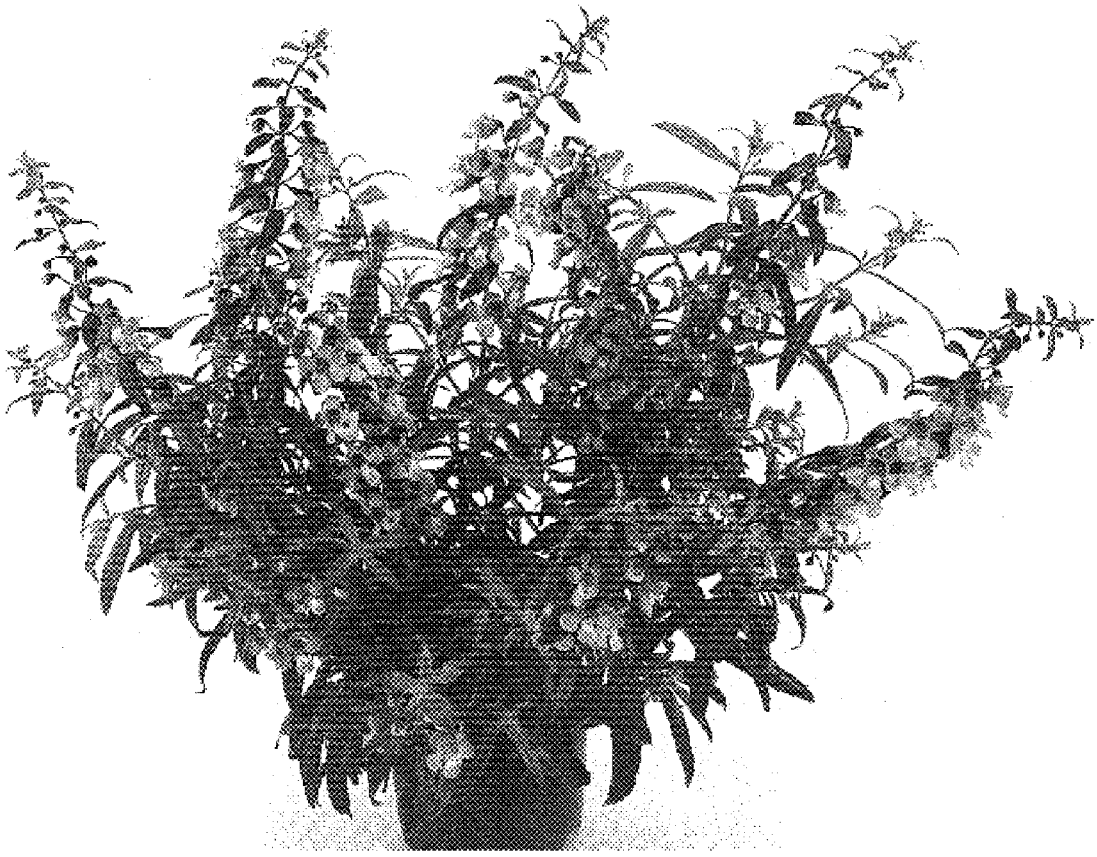

The accompanying photograph in FIG. 1 illustrates in full color a typical plant of 'DANGELONI3' grown in a greenhouse, in a 12 cm pot. Age of the plant photographed is approximately 3 months from a rooted cutting.

Figure 2:
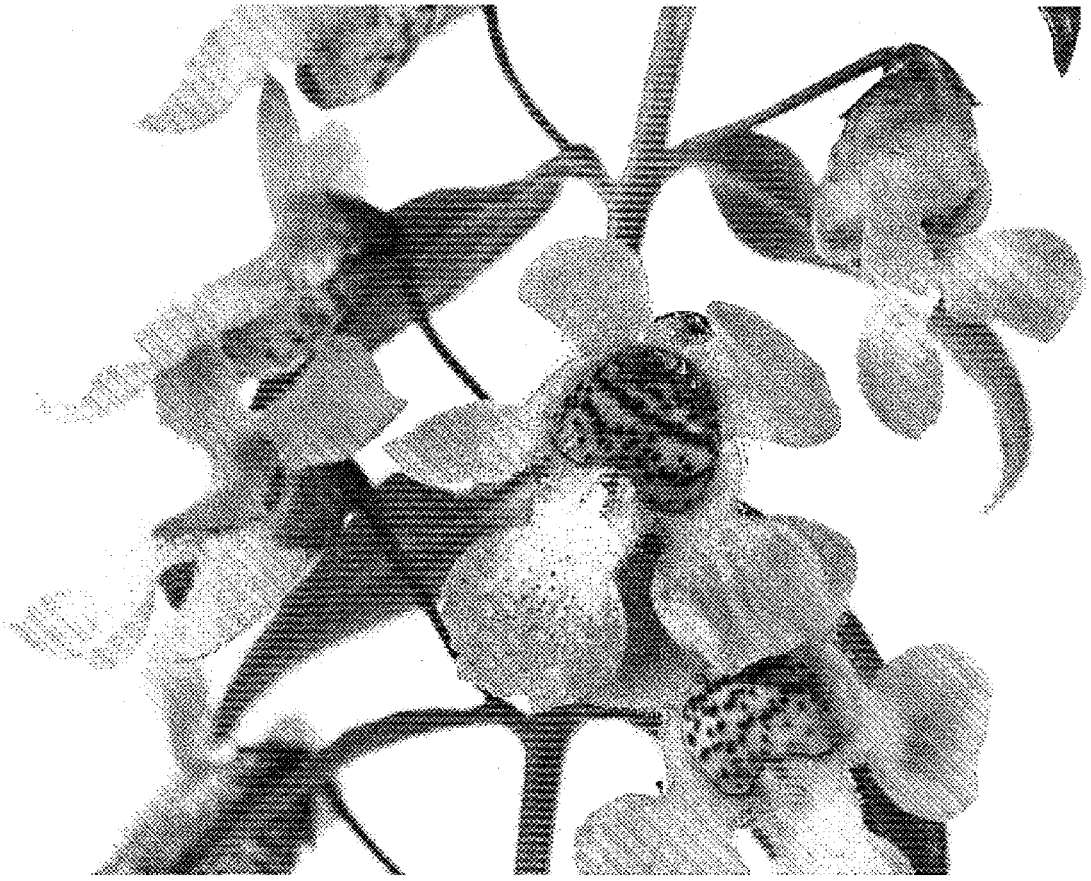

FIG. 2 illustrates in full color a close up of a typical bloom of 'DANGELONI3.'

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart except where general terms of ordinary dictionary significance are used. The following observations and measurements describe 'DANGELONI3' plants grown in a greenhouse in Moshav Mishmar Hashiva, Israel. The growing temperature ranged from 20° C. to 28° C. The greenhouse is un-shaded, giving bright, normal sunlight conditions. Measurements and numerical values represent averages of typical plant types.

Botanical classification: *Angelonia angustifolia* cultivar 'DANGELONI3'.

PROPAGATION

Time to initiate roots: About 14 days at approximately 25° C.
Root description: Fine, densely fibrous.
Time to produce a rooted cutting: About 35 days at 25° C.

PLANT

Growth habit: Upright, erect annual.
Pot size of plant described: 10 cm.
Height:
*To top of foliage.*—Approximately 16 cm.
*To top of racemose.*—Approximately 31 cm.
Plant spread: Approximately 14 cm.
Growth rate: Rapid.
Branching characteristics: Well-branched, all branches occurring at an acute angle, forming an upright plant shape.
Length of primary lateral branches: Approximately 16 cm.
Diameter of lateral branches: Approximately 0.2 cm.
Quantity of lateral branches: Numerous, more than 10.
Stem:
*Form.*—Round in cross-section.
*Color.*—Near RHS Yellow-Green 144 B.
*Texture.*—Smooth.
Internode length: Approximately 0.2 cm.
Age of plant described: Approximately 45 days from a rooted cutting.

FOLIAGE

Leaf:
*Arrangement.*—Opposite.
*Quantity.*—Approximately 32 per main branch.
*Average length.*—Approximately 4 cm.
*Average width.*—Approximately 0.7 cm.
*Shape of blade.*—Linear.
*Apex.*—Acute.
*Base.*—Cuneate.
*Attachment.*—Sessile.
*Margin.*—Serrate.
*Texture of top surface.*—Matte.
*Pubescence.*—Slightly pubescent.
*Color.*—Young foliage upper side: Near RHS Green 143A. Young foliage under side: Near RHS Green 143C. Mature foliage upper side: Near RHS Green 137A. Mature foliage under side: Near RHS Green 137C.
*Venation.*—Type: Pinnate. Venation color upper side: Near RHS Green 137A. Venation color under side: Near RHS Green 137C.
*Petiole.*—Not Present.

FLOWER

Natural flowering season: Freely flowering under outdoors growing conditions with substantially continuous blooming from spring through autumn. Year round in greenhouse environment, or under warm conditions and high sunlight. Begins flowering approximately 5 weeks after planting a rooted cutting.
Inflorescence and flower type and habit: Individual flowers are typical scrophulariaceae shape, 2-lipped, 5-petaled solitary flowers, fused at base, occurring in the leaf axis, on a terminal raceme.
Rate of flowering opening: 5 to 10 days from bud to fully opened flower.
Flower longevity on plant: Individual flowers last approximately 10 days on the plant. Each spike lasts approximately 2 weeks with flowers.
Quantity of flowers: About 16 to 30 florets per spike.
Flower size:
*Diameter.*—Approximately 2 cm.
*Length.*—Approximately 2 cm.
Petals:
*Length.*—1 cm.
*Diameter.*—1 cm.
*Quantity.*—5.
*Texture.*—Papillose.
*Color.*—When opening: Upper surface: Near RHS Red-Purple 70D. Lower surface: Near RHS Red-Purple 70D. Fully opened: Upper surface: Near RHS Red-Purple 70C. Lower surface: Near RHS Red-Purple 70C.
Bud:
*Shape.*—Orbicular.
*Length.*—Approximately 0.5 cm.
*Diameter.*—Approximately 0.5 cm.
*Color.*—Near RHS Yellow 2A.
Sepals:
*Quantity per flower.*—5, fused at base.
*Shape.*—Ovate.
*Length.*—Approximately 0.3 cm.
*Width.*—Approximately 0.1 cm.
*Apex.*—Acute.
*Base.*—Cuneate.
*Margin.*—Entire.
*Texture.*—Glabrous.
*Color.*—Near RHS Green 143A.
Peduncle: None.
Pedicel:
*Length.*—Approximately 0.7 cm.
*Diameter.*—Approximately 0.1 cm.
*Color.*—Near RHS Purple N77A.
Fragrance: None.

REPRODUCTIVE ORGANS

Stamens:
*Number.*—4, occurring in pairs.
*Filament length.*—Approximately 0.1 cm.
Anthers:
*Shape.*—Ovoid.
*Length.*—Approximately 1 mm.
*Color.*—Near RHS Yellow 2C.
*Pollen.*—Color: Near RHS Greyed-Yellow 161A. Quantity: Moderate.
Pistil:
*Number.*—1.
*Length.*—Approximately 0.2 cm.
*Style.*—Length: Approximately 0.15 cm. Color: Pure white.
*Stigma.*—Shape: Round. Color: Near RHS Yellow 2D.

OTHER CHARACTERISTICS

Seeds and fruits: Not observed and not commercially important.
Disease/pest resistance: Neither resistance nor susceptibility to pathogens and pests common to *Angelonia* have been observed.
Temperature tolerance: The new variety tolerates temperatures between 8 to 35° C.

What is claimed is:

1. A new and distinct cultivar of *Angelonia* plant named 'DANGELONI3' as herein illustrated and described.

* * * * *